(12) United States Patent
Miyamoto et al.

(10) Patent No.: US 8,092,470 B2
(45) Date of Patent: Jan. 10, 2012

(54) CALCULUS CRUSHING APPARATUS AND MEDICAL PROCEDURE USING ENDOSCOPE

(75) Inventors: Satoshi Miyamoto, Tokyo (JP); Takehiro Nishiie, Tokyo (JP); Junichi Kobayashi, Fujinomiya (JP); Yasushi Kinoshita, Fujinomiya (JP)

(73) Assignees: Olympus Medical Systems Corp., Tokyo (JP); Terumo Kabushiki Kaisha, Tokyo (JP)

( * ) Notice: Subject to any disclaimer, the term of this patent is extended or adjusted under 35 U.S.C. 154(b) by 1073 days.

(21) Appl. No.: 11/449,542

(22) Filed: Jun. 8, 2006

(65) Prior Publication Data

US 2008/0033467 A1 Feb. 7, 2008

(51) Int. Cl.
*A61B 17/22* (2006.01)
(52) U.S. Cl. ......... 606/128; 606/114; 606/127; 606/200
(58) Field of Classification Search .................. 606/127, 606/128, 114, 200
See application file for complete search history.

(56) References Cited

U.S. PATENT DOCUMENTS

| 6,146,395 | A | 11/2000 | Kanz et al. |
| 6,383,195 | B1 | 5/2002 | Richard |
| 2003/0187468 | A1 | 10/2003 | Shiber |
| 2004/0082962 | A1* | 4/2004 | Demarais et al. ............. 606/128 |
| 2005/0059981 | A1 | 3/2005 | Poll |

FOREIGN PATENT DOCUMENTS

| EP | 0 426 322 A1 | 5/1991 |
| EP | 0 533 320 A2 | 3/1993 |
| EP | 0 328 628 B1 | 11/1995 |
| JP | 3-56416 | 5/1991 |
| JP | 2000-333967 | 12/2000 |

OTHER PUBLICATIONS

Ruzzu et al. "A Cutter wtih Rotational-Speed Dependent Diameter for Interventional Catheter Systems", 1998.*

Ruzzu, A., et al., "A Cutter with Rotational-Speed Dependent Diameter for Interventional Catheter Systems", Micro Electro Mechanical Systems, 1998 Mems 98. Proceedings, The Eleventh Annual International Workshop on Heidelberg, Germany Jan. 25-29, 1998, New York, NY USA, IEEE US Jan. 25, 1998, pp. 499-503, XP010270204 ISBN: 0-7803-4412-X * the whole document *.

* cited by examiner

*Primary Examiner* — Gary Jackson
*Assistant Examiner* — Kevin Everage
(74) *Attorney, Agent, or Firm* — Scully, Scott, Murphy & Presser, P.C.

(57) ABSTRACT

An apparatus includes a crushing part which rotates and crushes the calculus, wherein a radius of rotation of the crushing part with respect to a rotation axis thereof increases or decreases in accordance with a rotation speed of the crushing part.

15 Claims, 20 Drawing Sheets

CALCULUS CRUSHING APPARATUS AND MEDICAL PROCEDURE USING ENDOSCOPE

BACKGROUND OF THE INVENTION

1. Field of the Invention

The present invention relates to a calculus crushing apparatus and a medical procedure using an endoscope.

2. Description of the Related Art

In order to remove a swelling calculus inside a bile duct in a stone crushing and collecting treatment, basket forceps may be inserted into the bile duct so as to catch the calculus using a deployed basket, and to physically cut the calculus by pushing basket wires onto the calculus. These basket wires are relatively thick so as to cut a hard stone.

If the calculus obtained by one cutting operation is too large to be extracted through a duodenal papilla, a similar operation by deploying the basket is repeated. When the cut calculus obtains a size at which it can be extracted through the papilla, the calculus is caught inside the basket and scraped out toward the duodenum, or is scraped out using a specialized basket or balloon specifically used for stone collection.

SUMMARY OF THE INVENTION

An object of the present invention is to provide a calculus crushing apparatus and a medical procedure using an endoscope, by which the calculus can be crushed in a single operation to obtain a size at which extraction through the duodenal papilla is possible, thereby allowing easily collection of cut stones and shortening of the treatment time.

An apparatus for crushing a calculus, as a first form of the present invention, has a crushing part which rotates and crushes the calculus, wherein a radius of rotation of the crushing part with respect to a rotation axis thereof increases or decreases in accordance with a rotation speed of the crushing part.

An apparatus for crushing a calculus, as a second form of the present invention, has a crushing part arranged along a central axis, which has a loop shape and rotates around the central axis so as to crush the calculus, wherein a diameter of the loop shape increases or decreases in accordance with a rotation speed of the crushing part.

An apparatus for crushing a calculus, as a third form of the present invention, has a crushing part which is formed by combining flexible shaft members and is rotatable around a central axis of the shaft members, wherein head portions of the shaft members freely contact and are away from the central axis in accordance with a rotation speed of the crushing part, and are formed to bend in outward radial direction.

An apparatus for crushing a calculus, as a fourth form of the present invention, has a crushing part having:
- a base portion which is arranged along a central axis and rotates around the central axis; and
- cutting pieces, each having one end connected to a head portion of the base portion, and the other end extending toward a base end side of the base portion in a manner such that the cutting piece and the base portion form an acute angle, wherein the acute angle between the base portion and each cutting piece varies in accordance with a rotation speed of the base portion.

An apparatus for crushing a calculus, as a fifth form of the present invention, has a crushing part extending like a shaft and having a head portion which has an eccentric axis away from a central axis of the shaft and rotates around the central axis, wherein an angle between the eccentric axis and the central axis increases or decreases in accordance with a rotation speed of the crushing part.

A medical procedure using an endoscope, as a first form of the medical procedure of the present invention, has the steps of:
inserting a sheath from a duodenal papilla into a bile or pancreatic duct, wherein the sheath contains a crushing part which rotates so as to cut a calculus in the bile or pancreatic duct, and in accordance with progress in the cutting of the calculus, the crushing part proceeds while increasing a radius of the cutting;
inserting a head of the sheath up to a position where the calculus can be held in the bile or pancreatic duct;
holding the calculus using a holding part which surrounds the calculus and supports the calculus with respect to the crushing part; and
crushing the calculus using the crushing part.

PREFERRED EMBODIMENTS OF THE INVENTION

Figure 1:
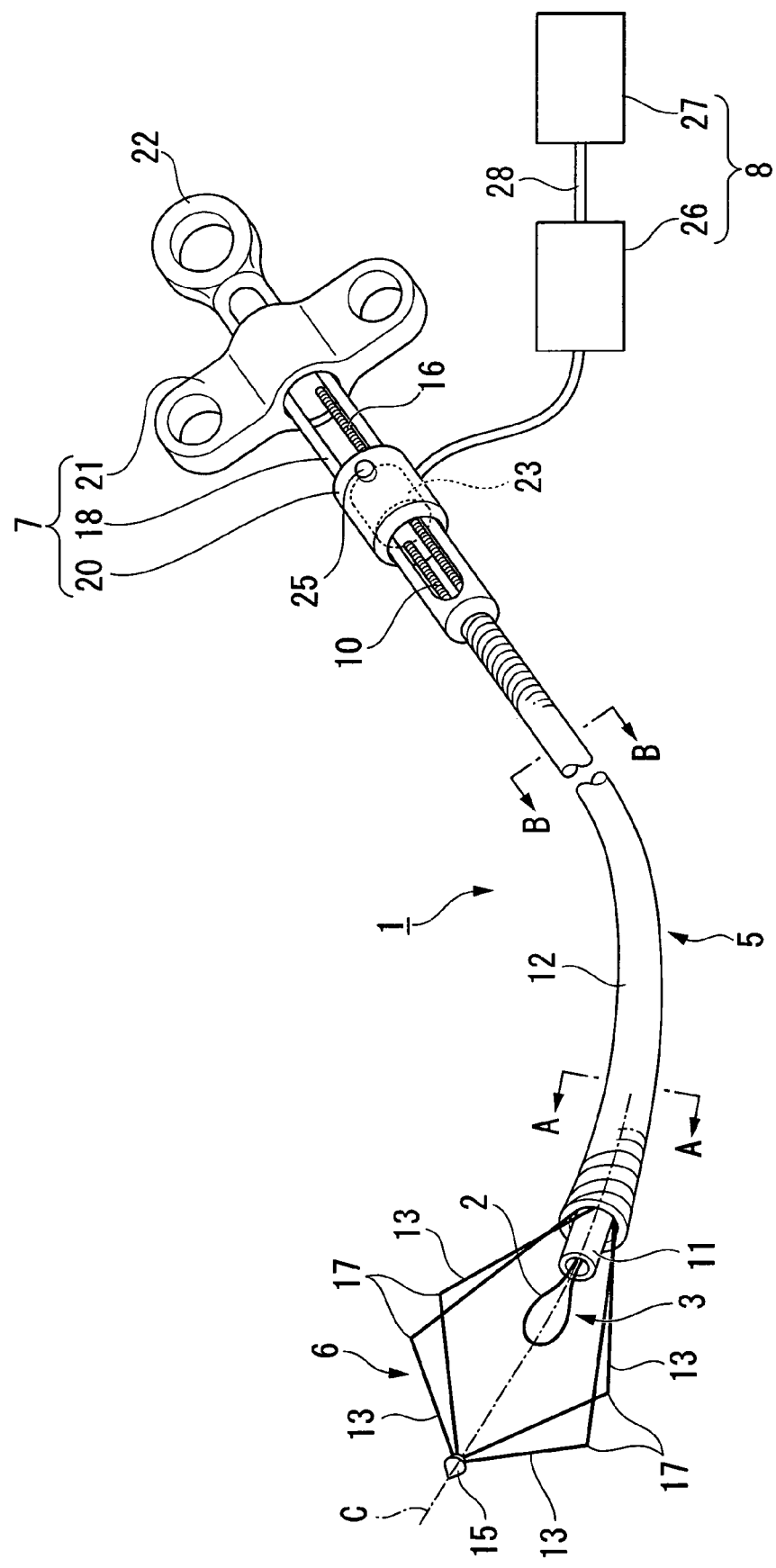
FIG. 1 is a diagram showing the general structure of a calculus crushing apparatus as a first embodiment.

Preferred embodiments of the present invention will be explained in detail below. In the following explanations, identical structural elements are given an identical reference numeral, and duplicated explanations are omitted.

First Embodiment

Figure 2:
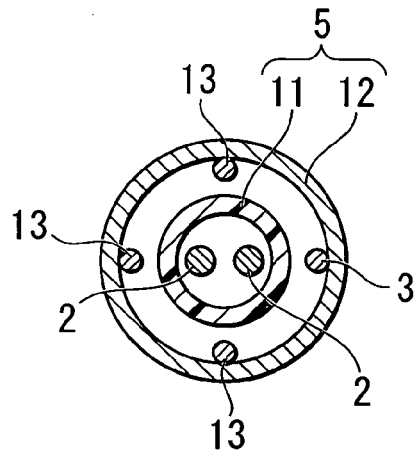
FIG. 2 is a sectional view along line A-A in FIG. 1.
Figure 3:
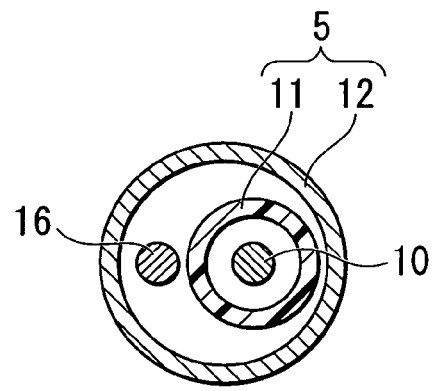
FIG. 3 is a sectional view along line B-B in FIG. 1.

As shown in FIGS. 1 to 3, a calculus crushing apparatus 1 in accordance with the present invention has a crushing part 3 which consists of a looped crushing wire 2 provided along a central axis C and is rotatable around the central axis C so as to crush a calculus, a sheath 5 for containing the crushing part 3 in a manner such that the crushing part 3 can protrude from the front end thereof in accordance with the rotation of the crushing part 3, a basket part 6 (i.e., a holding part) for surrounding the crushing part 3 and supporting the calculus with respect to the crushing part 3, an operation part 7 for rotating the crushing part 3 and deploying and folding the basket part 6, and a power supply part 8 for supplying a driving force to the crushing part 3. Liquid such as water or a gas such as air can function as the driving force. The calculus may be formed in a bile duct, a pancreatic duct, urinary duct, gall bladder, urinary bladder, kidney, or the like.

The sheath 5 has an internal sheath 11 for containing the crushing part 3 and a crushing part operating wire 10 in a freely slidable (i.e., they can be freely advanced or withdrawn) and rotatable manner, and an external sheath 12 for containing the internal sheath 11 in a freely rotatable manner and also containing the basket part 6, provided outside the internal sheath 11, in a freely slidable manner.

The crushing wire 2 of the crushing part 3 is made of metal, and preferably, a stainless steel. However, the crushing wire 2 may be made of an Ni—Ti alloy or a Ti alloy, or may also be made of resin, or made using a combination of metal and resin. Preferably, a material which can be detected in X-ray filming (or observation) is provided at least at the front end of the crushing wire 2.

Figure 4:
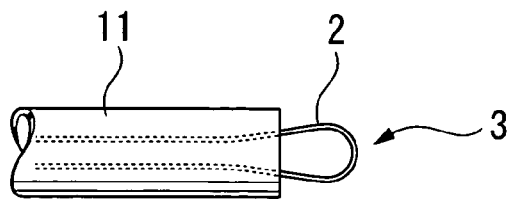
FIG. 4 is a plan view showing the crushing part of the calculus crushing apparatus of the first embodiment.
Figure 5:
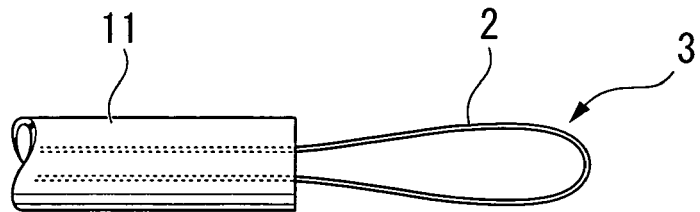
FIG. 5 is also a plan view showing the crushing part of the calculus crushing apparatus of the first embodiment.

Both ends of the crushing part 3 are connected to the crushing part operating wire 10. Therefore, when the crushing part operating wire 10 advances or withdraws with respect to the internal sheath 11, the crushing part 3 also advances or withdraws with respect to the internal sheath 11, as shown in FIGS. 4 and 5.

Figure 6:
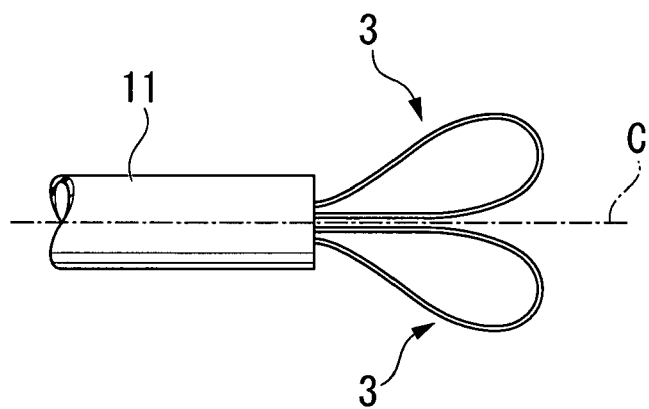
FIG. 6 is a plan view showing the crushing part of a variation of the calculus crushing apparatus of the first embodiment.
Figure 7:
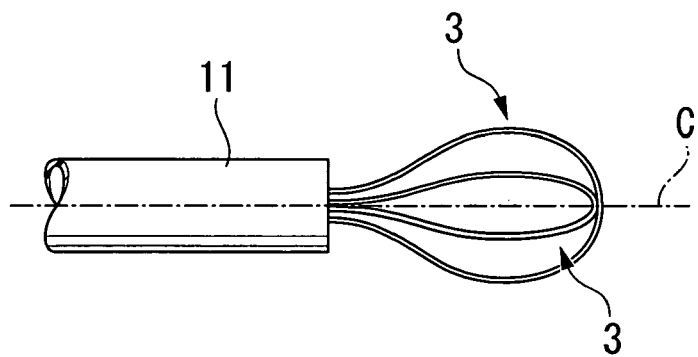
FIG. 7 is a plan view showing the crushing part of another variation of the calculus crushing apparatus of the first embodiment.

The crushing part 3 can contract and be contained in the internal sheath 11. When protruding from the internal sheath 11, the crushing part 3 elastically changes its shape so that the crushing part 3 is deployed and obtains a size larger than the internal sheath 11. As shown in FIGS. 6 and 7, a plurality of the crushing parts 3 may be provided. Such crushing parts 3 may be arranged within the same plane, or be respectively arranged in planes intersecting each other. It is preferable to further provide a member for suppressing abrasion or excessive heat due to contact between the crushing wire 2 and the calculus when the crushing part 3 rotates, on the front end side of the internal sheath 11.

As shown in FIG. 1, the basket part 6 has a plurality of basket wires 13, whose heads are combined using a head tip 15. Each wire 13 extends along the inside of the outer sheath 12 toward the base end thereof, and the wires 13 are combined and connected to a holding operation wire 16 which is arranged inside the outer sheath 12 along the internal sheath 11. Each basket wire 13 has a bending point 17, and is contained inside the outer sheath 12 when it is bent outward (to be stretched) at the bending point 17. When this bent state with respect to the bending point 17 is released, the basket wires 13 are deployed. Preferably, the head tip 15 is made of a material which can be detected in X-ray filming.

As shown in FIG. 1, the operation part 7 has an operation part main body 18 extending along the central axis C of the sheath 5, and a crushing part slider 20 and a holding slider 21 which are freely slidable along the axis of the operation part main body 18.

The operation part main body 18 is connected to the base end of the outer sheath 12, and a finger catcher 22 is provided at the base end of the operation part main body 18. A motor 23 for rotating the crushing part operating wire 10 with respect to the internal sheath 11, and a hand switch 25 for switching on and off the motor 23 are provided to the crushing part slider 20. The motor 23 is connected to the base end of the crushing part operating wire 10. The base end of the holding operation wire 16 is connected to the holding slider 21, and the finger catcher 22 is arranged near the holding slider 21.

As shown in FIG. 1, the power supply part 8 has a power source 26 for supplying driving power to the motor 23 and a foot switch 27 for switching on and off the power source 26. These elements are electrically connected via electric wiring 28.

Next, the operation of the calculus crushing apparatus 1 of the present embodiment will be explained together with medical treatment (i.e., procedure) using an endoscope and this apparatus. In an example of the medical treatment explained below, a catheter (not shown) for a contrast media is inserted into a duodenal papilla P by using an endoscope 30 so as to inject the contrast media into a bile duct BD, and diagnosis using X-ray radiography is performed so as to remove calculi around the bile duct.

The medical procedure using the endoscope of the present embodiment includes a step of inserting the sheath 5 from the duodenal papilla P into the bile duct BD; a step of inserting the head of the sheath 5 up to a position where a calculus CH can be held in the bile duct BD (in the present embodiment, this position is ahead of the calculus CH); a step of holding the calculus CH using the basket part 6 which surrounds the crushing part 3 and supports the calculus CH with respect to the crushing part 3; a step of crushing the calculus CH using the crushing part 3; and a step of collecting the crushed calculus CH.

First, an insertion part 33 of the endoscope 3 is inserted into the mouth of a patient (not shown), and the head of the insertion part 33 is positioned in the vicinity of the duodenal papilla P via the esophagus (not shown). The operation for adjusting the angle and the torsion state of the endoscope 30 is then performed so that the head opening of a channel (not shown) of the endoscope 30 is opposed to the duodenal papilla P.

Figure 8:
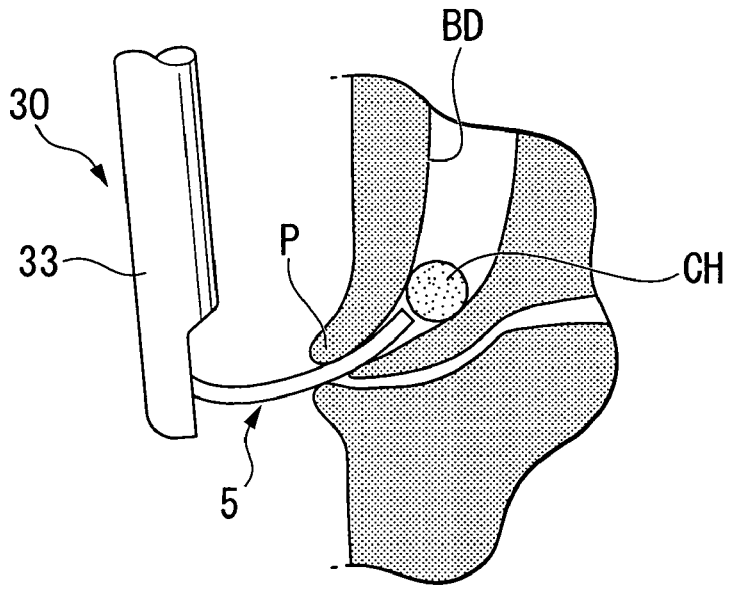
FIG. 8 is a diagram explaining an example of use of the calculus crushing apparatus of the first embodiment.
Figure 9:
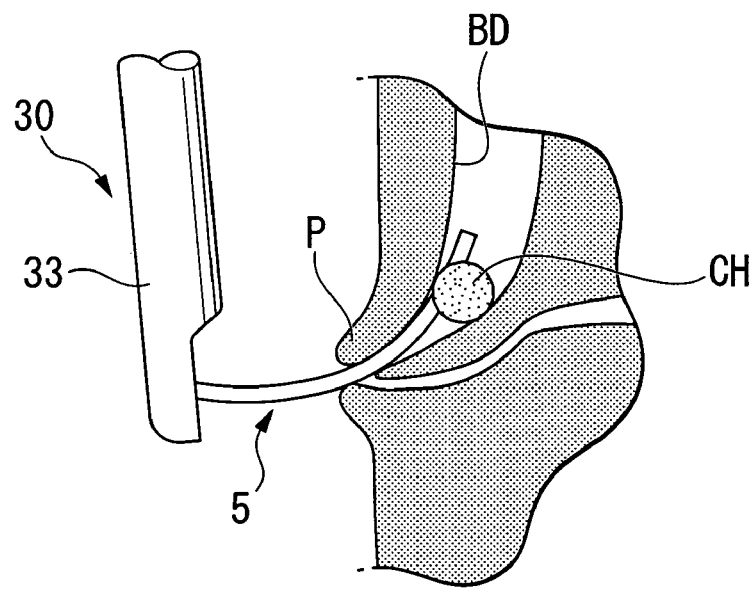
FIG. 9 is also a diagram explaining the example of use of the calculus crushing apparatus of the first embodiment.

Next, the sheath 5 of the above-described calculus crushing apparatus 1 is inserted from a forceps opening (not shown) of the endoscope 30 into this channel so that the sheath 5 protrudes from the head opening of the channel and is inserted from the duodenal papilla P into the bile duct BD (see FIG. 8). In this process, the head of the sheath 5 is made to reach a position ahead of the calculus CH while performing X-ray radiography (see FIG. 9).

Figure 10:
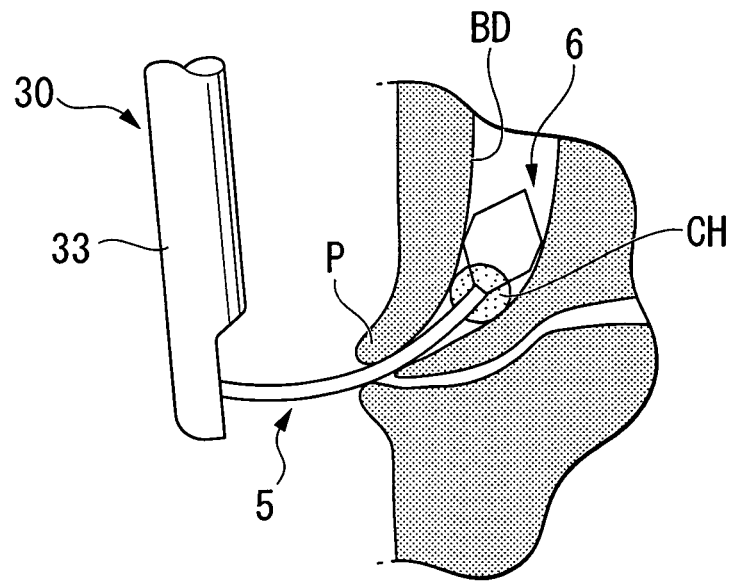
FIG. 10 is also a diagram explaining the example of use of the calculus crushing apparatus of the first embodiment.
Figure 11:
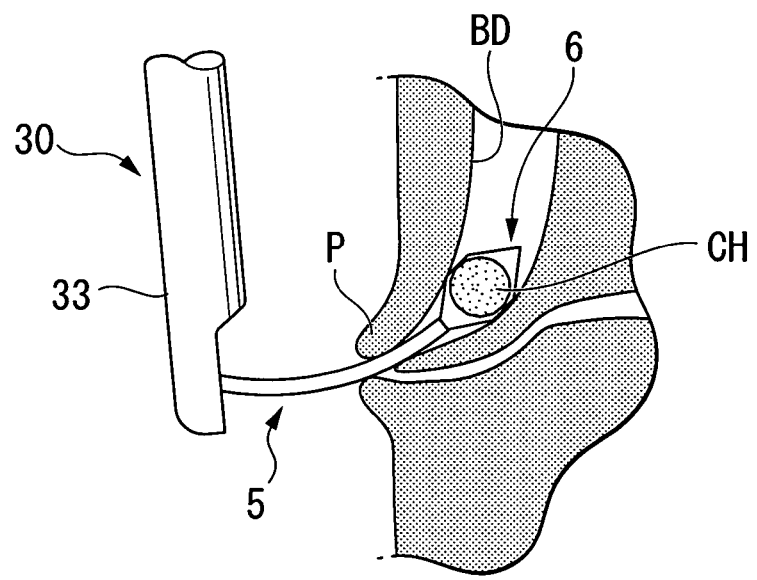
FIG. 11 is also a diagram explaining the example of use of the calculus crushing apparatus of the first embodiment.

In this state, an operator (not shown) holds the holding slider 21 of the operation part 7, and advances the slider 21 with respect to the operation part main body 18 while confirming the present state using an observation image. In this process, the basket part 6 protrudes from the head of the sheath 5 towards the inside of the bile duct BD and is deployed (see FIG. 10). The calculus CH is caught inside the deployed basket part 6 by withdrawing the basket part 6 together with the sheath 5 towards the operator's hand (see FIG. 11). In addition, the basket part 6 is contracted by withdrawing the holding slider 21 with respect to the operation part main body 18 so that the calculus CH is supported with respect to the sheath 5 while the head of the crushing part 3 contacts the calculus CH.

Figure 12:
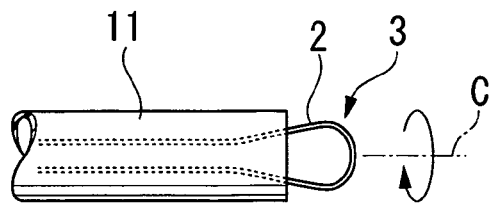
FIG. 12 is also a diagram explaining the example of use of the calculus crushing apparatus of the first embodiment.
Figure 13:
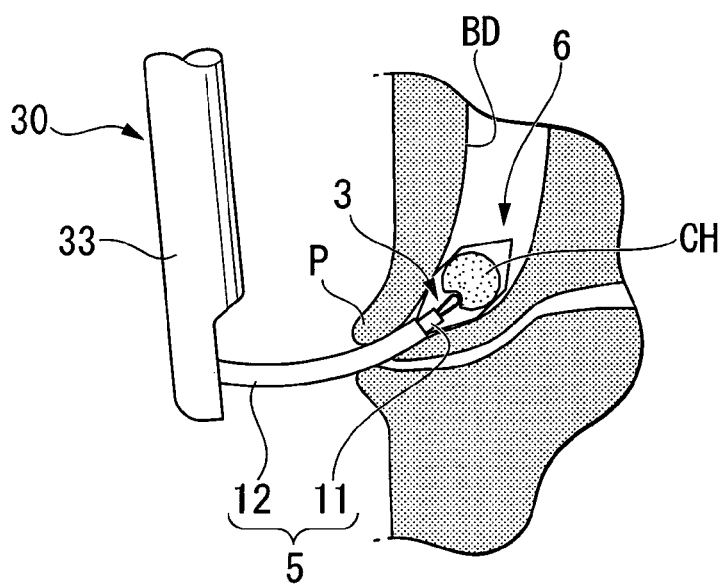
FIG. 13 is also a diagram explaining the example of use of the calculus crushing apparatus of the first embodiment.

After the foot switch 27 of the power supply part 8 is turned on, the hand switch 25 of the crushing part slider 20 is turned on. In this process, the motor 23 is operated so as to rotate the crushing part operating wire 10 with respect to the internal sheath 11, and also to rotate the crushing part 3 (see FIG. 12), thereby cutting a portion of the calculus CH, which the crushing part 3 contacts (see FIG. 13).

Figure 14:
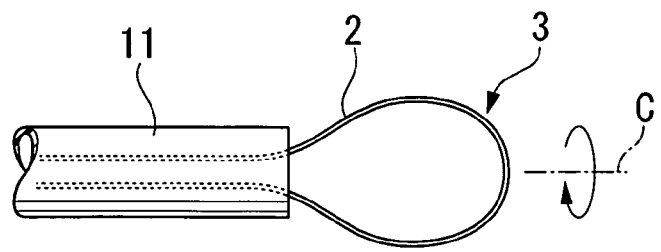
FIG. 14 is also a diagram explaining the example of use of the calculus crushing apparatus of the first embodiment.
Figure 15:
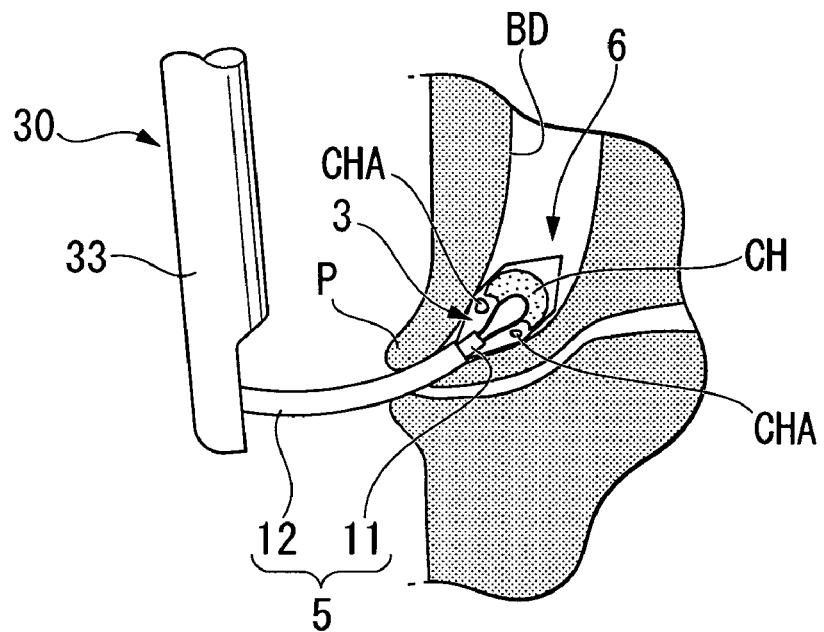
FIG. 15 is also a diagram explaining the example of use of the calculus crushing apparatus of the first embodiment.
Figure 16:
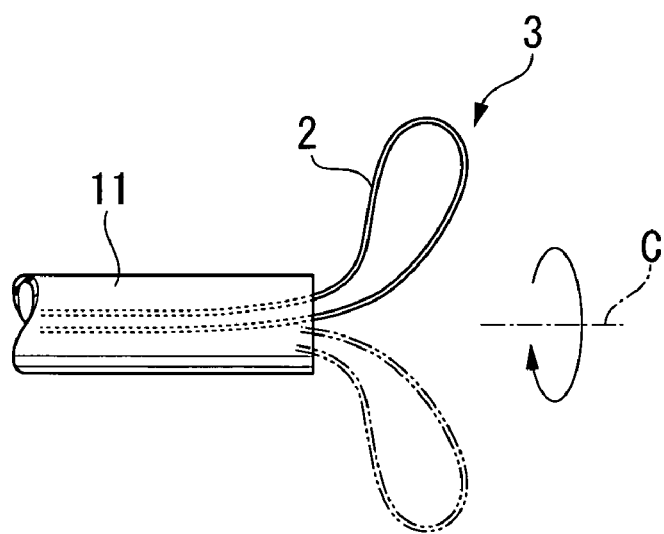
FIG. 16 is also a diagram explaining the example of use of the calculus crushing apparatus of the first embodiment.

When the rotation speed of the motor 23 is increased, a centrifugal force is applied to the crushing wire 2 of the crushing part 3 in outward radial directions. Therefore, as this centrifugal force increases, the diameter of the loop of the crushing part 3 also increases towards directions perpendicular to the central axis C (see FIG. 14). Accompanied with this operation, the crushing part operating wire 10 protrudes from the internal sheath 11 so that the entire crushing part 3 further protrudes with respect to the internal sheath 11. In this process, the crushing part slider 20 may be voluntarily advanced with respect to the operation part main body 18. Accordingly, as shown in FIG. 15, cutting of the calculus CH further proceeds. When the above rotation speed is increased, the crushing part 3 itself rotates around the central axis C as shown in FIG. 16; thus, the possible diameter for the cutting operation further increases.

Figure 17:
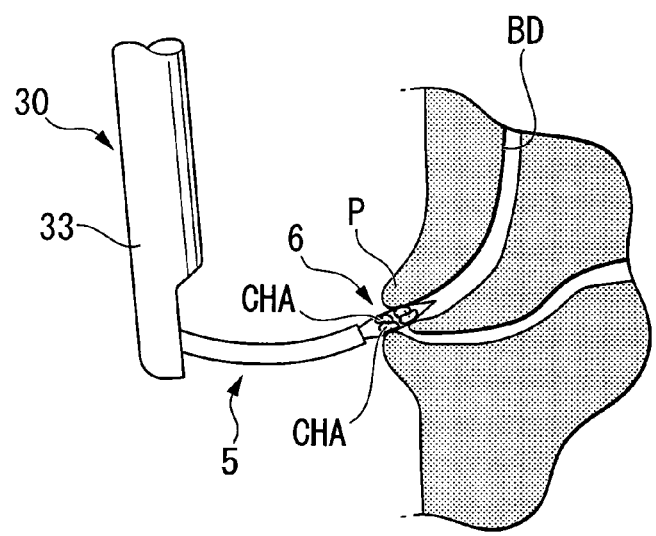
FIG. 17 is also a diagram explaining the example of use of the calculus crushing apparatus of the first embodiment.

After the calculus CH is cut into smaller calculus pieces CHA, the hand switch 25 and the foot switch 27 each are turned off so that the rotation of the motor 23 is stopped. Then the crushing part slider 20 is withdrawn with respect to the operation part main body 18 so as to contain the crushing part 3 inside the internal sheath 11. Simultaneously, the holding slider 21 is withdrawn with respect to the operation part main body 18 so as to contact the basket part 6 and hold the calculus pieces CHA. Accordingly, as shown in FIG. 17, the calculus pieces CHA are collected through the duodenal papilla P by withdrawing the sheath 5 toward the operator's hand.

In the collection, the pieces are suctioned using a suction source (not shown) through gaps between the outer sheath 12, the inner sheath 11, and the holding operation wire 16. Alternatively, the inner sheath 11 and the holding operation wire 16 are pulled out and removed from the outer sheath 12, and the pieces are suctioned through an inner hole formed in the outer sheath 12. In another example, the entire calculus crushing apparatus 1 including the outer sheath 12, the inner sheath 11, and the holding operation wire 16 is removed and a suction catheter (not shown) is inserted instead so as to suction the pieces. However, if the calculus is cut into fine pieces, they are naturally discharged from the bile duct BD without performing a collection step.

In accordance with the calculus crushing apparatus 1, the radius for cutting the calculus CH can be increased or decreased by increasing or decreasing the rotation speed (i.e., the radius of rotation) of the crushing part 3. Therefore, the calculus CH can be cut into pieces which can be removed from the duodenal papilla P in a single operation, thereby easily collecting the cut pieces, reducing the number of times of insertion or removal of stone crushing or treatment tools, and shortening the treatment time.

Additionally, due to the centrifugal force applied to the crushing part 3, the head side of the crushing part 3 receives a force acting in an outward radial direction; thus, the crushing part 3 can be automatically protruded from the internal sheath 11 without positively operating the crushing part operating wire 10.

In addition, when the crushing part 3 is not rotated, the crushing part 3 can be contained inside the internal sheath 11.

Furthermore, during the crushing, the calculus CH is held using the basket part 6; thus, it is possible to preferably prevent the calculus CH from rotating together with the crushing part 3.

Second Embodiment

Figure 18:
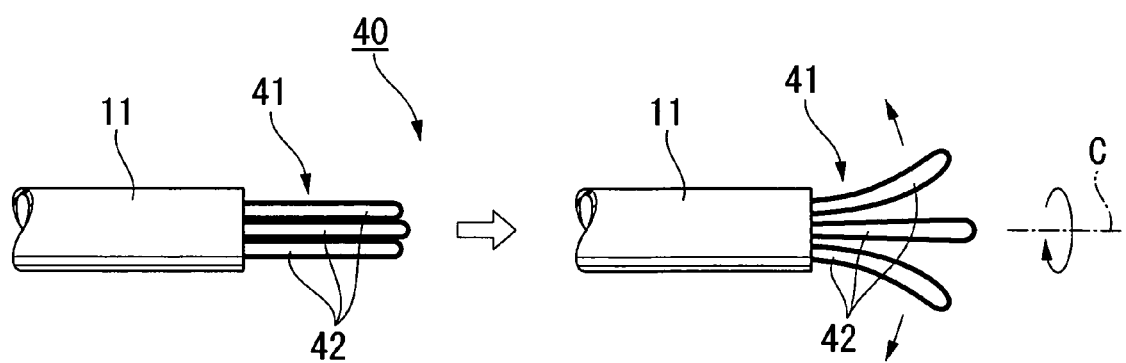
FIG. 18 is a plan view showing the crushing part of the calculus crushing apparatus of a second embodiment.

A second embodiment of the present invention will be explained with reference to the drawings. In comparison with the first embodiment, a calculus crushing apparatus 40 of the present embodiment has distinctive features (see FIG. 18) in which a crushing part 41 consists of a plurality of linear-shaped flexible shaft members 42 which are combined and rotatable around the central axis C, and the heads of the shaft members 42 can freely contact or be separated from the central axis C and are bent in outward radial directions. In this case, the shaft members 42 are combined in a freely slidable manner inside the internal sheath 11. The base end of each shaft member 42 is connected to a crushing part operating wire (not shown).

Next, the operation of the calculus crushing apparatus 40 of the present embodiment will be explained, similar to the first embodiment.

First, an insertion part of the endoscope (not shown) is inserted in to the vicinity of the duodenal papilla, and the head of the insertion part is positioned. Then, the operation for adjusting the angle and the torsion state of the endoscope is performed so that the head opening of a channel (not shown) of the endoscope is opposed to the duodenal papilla.

Next, the sheath of the above-described calculus crushing apparatus 40 is inserted into the channel (not shown) so that the sheath protrudes from the head opening of the channel and is inserted from the duodenal papilla into the bile duct. In the next step, a basket part (not shown) is deployed so as to hold a calculus (not shown). In this state, a crushing slider (not shown) is advanced with respect to an operation part main body (not shown) so that the shaft members 42 protrude from the internal sheath 11 by a predetermined length. In this state, a motor (not shown) is operated so as to rotate a crushing part operating wire (not shown) around the axis with respect to the internal sheath 11 and also rotate the crushing part 41. In this process, the head portions of the shaft members 42, which protrude from the internal sheath 11, are away from the central axis C in outward radial directions and separated from each other due to a centrifugal force accompanied with the rotation. Accordingly, portions of the calculus CH, which the heads of the shaft members 42 contact, are crushed.

In accordance with the calculus crushing apparatus 40, the centrifugal force applied to the heads of the shaft members 42 increases when the rotation speed of the motor is increased; thus, it is possible to increase the outer diameter of the head portion of the crushing part 41 with respect to the central axis C. Additionally, similar to the first embodiment, the shaft members 42 are pulled out from the internal sheath 11 so that the entire crushing part 41 further protrudes with respect to the internal sheath 11 so as to crush the calculus.

Third Embodiment

Figure 19:
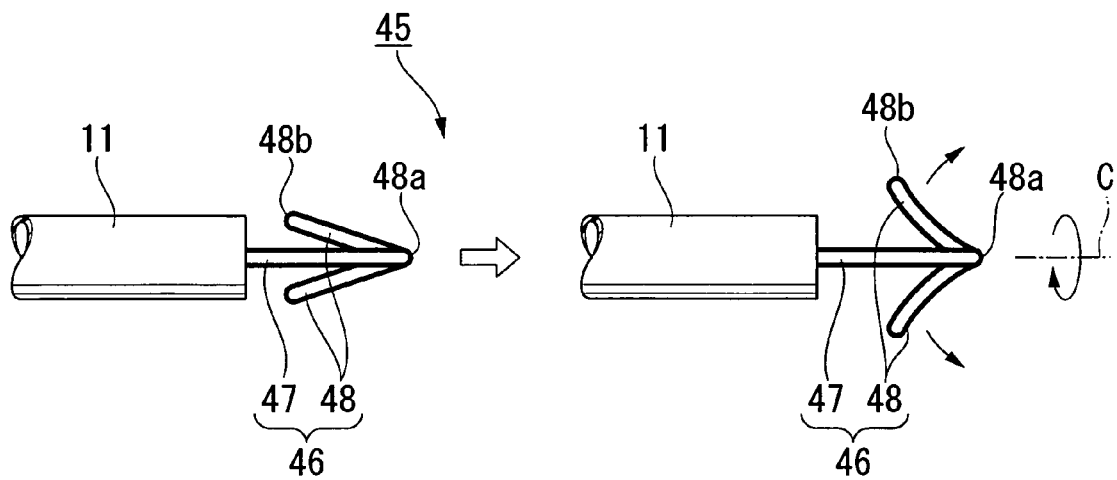
FIG. 19 is a plan view showing the crushing part of the calculus crushing apparatus of a third embodiment.

A third embodiment of the present invention will be explained with reference to the drawings. In comparison with the second embodiment, a calculus crushing apparatus 45 of the present embodiment has distinctive features (see FIG. 19) in which a crushing part 46 has a base portion 47 which extends along the central axis C and rotates around the central axis C, and a plurality of cutting pieces 48 like plate springs. One end 48a of each cutting piece 48 is connected to the head of the base portion 47, and the other end 48b extends along an axis which is inclined so as to form an acute angle between this axis and the base portion 47.

The base portion 47 is connected to a crushing part operating wire 10 (not shown). When being contained in the internal sheath 11, the cutting pieces 48 are pushed and elastically deformed so that they are substantially parallel to the base portion 47. When the cutting pieces 48 are protruded from the internal sheath 11, the restriction by the internal sheath 11 is released so that the cutting pieces 48 are inclined with respect to the base portion 47 by a predetermined angle.

Next, the operation of the calculus crushing apparatus 45 will be explained, similar to the above embodiments.

A crushing part slider (not shown) is advanced with respect to an operation part main body (not shown), so that the cutting pieces 48 are protruded from the internal sheath 11. Then the crushing part operating wire is rotated with respect to the internal sheath 11, and the crushing part 46 is also rotated. In this process, a centrifugal force accompanying the rotation is applied to the other ends 48b of the cutting pieces 48, so that the cutting pieces 48 are bent so as to be away from the central axis C and separated outward from each other in the radial directions. Accordingly, the outer diameter of the crushing part 46 increases and portions which contact the cutting pieces 48 are crushed. In addition, similar to other embodiments discussed above, the crushing part 46 further protrudes from the internal sheath 11 by increasing the rotation speed of the motor (not shown).

In accordance with the calculus crushing apparatus 45, the centrifugal force applied to the other ends 48b of the cutting pieces 48 increases when the rotation speed of the motor (not shown) is increased; thus, it is possible to increase the outer diameter of the crushing part 46 with respect to the central axis C. Additionally, similar to the above-described other embodiments, the base portion 47 is pulled out from the internal sheath 11 so that the entire crushing part 46 further protrudes with respect to the internal sheath 11 so as to crush the calculus.

Fourth Embodiment

Figure 20:
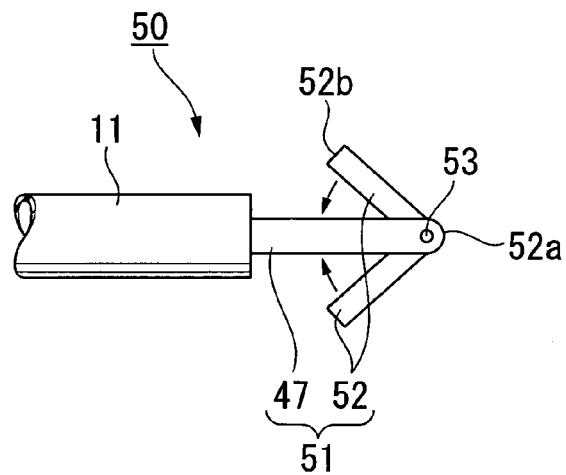
FIG. 20 is a plan view showing the crushing part of the calculus crushing apparatus of a fourth embodiment.

A fourth embodiment of the present invention will be explained with reference to the drawings. In comparison with the third embodiment, a calculus crushing apparatus 50 of the present embodiment has distinctive features (see FIG. 20) in which a crushing part 51 has cutting pieces 52, and one end of each cutting piece 52 is supported in a freely rotatable manner with respect to the base portion 47.

Each cutting piece 52 is not like a plate spring, has rigidity, and is connected to the base portion 47 via a pivot 53 in a freely rotatable manner. When being contained in the internal sheath 11, the cutting pieces 52 are pressed together with the base portion 47 in a manner such that both are substantially parallel to each other.

The operation of the calculus crushing apparatus 50 will be explained, similar to the above embodiments.

First, the cutting pieces 52 are protruded from the internal sheath 11, in accordance with an operation similar to that in the third embodiment. In this state, the crushing part operating wire 10 is rotated around the axis with respect to the internal sheath 11, and the crushing part 51 is also rotated.

In this process, a centrifugal force accompanying the rotation is applied to the other ends 52b of the cutting pieces 52 which protrude from the internal sheath 11, so that the other ends 52b rotate around the end 52a as the center of the rotation so as to be separated outward from the central axis C. Accordingly, the outer diameter of the crushing part 51 increases in directions perpendicular to the central axis C, and portions of the calculus which contact the cutting pieces 52 are crushed. In addition, similar to other embodiments discussed above, the crushing part 51 further protrudes from the internal sheath 11 by increasing the rotation speed of the motor (not shown).

In accordance with the calculus crushing apparatus 51, effects similar to those obtained by the third embodiment can be obtained.

Fifth Embodiment

Figure 21:
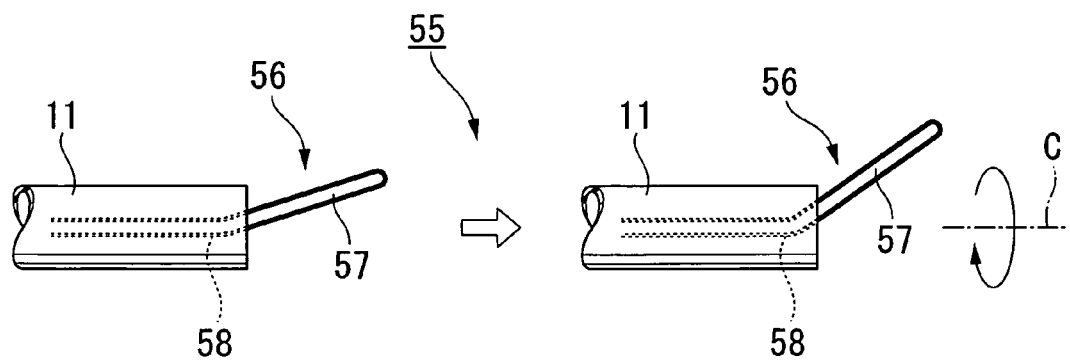
FIG. 21 is a plan view showing the crushing part of the calculus crushing apparatus of a fifth embodiment.

A fifth embodiment of the present invention will be explained with reference to the drawings. In comparison with the first embodiment, a calculus crushing apparatus 55 of the present embodiment has distinctive features (see FIG. 21) in which a crushing part 56 is formed using a flexible shaft member 57 having a head portion whose axis is away from the central axis C, and this head portion rotates around the central axis C.

Specifically, the shaft member 57 is bent at a bending portion 58 so as to be inclined with respect to the central axis C by a specific angle. The shaft member 57 is flexible; thus, when being contained in the internal sheath 11, the shaft member 57 is bent at the bending portion 58 so that the head side is stretched along the central axis C. The base end of the shaft member 57 is connected to a crushing part operating wire (not shown).

The operation of the calculus crushing apparatus 55 will be explained, similar to the above-described other embodiments.

First, similar to the other embodiments, the head side of the shaft member 57 is protruded from the internal sheath 11. In this state, a motor (not shown) is operated so as to rotate the crushing part operating wire (not shown) around the axis with respect to the internal sheath 11, and also to rotate the crushing part 56.

In this process, a centrifugal force accompanying the rotation is applied to the head side of the crushing part 56 with respect to the bending portion 58, which protrudes from the internal sheath 11, so that this head side is bent so as to be further away from the central axis C, and the outer diameter of the crushing part 56 increases in directions perpendicular to the central axis C. Accordingly, portions of the calculus which contact the cutting pieces 56 are crushed. In addition, similar to other embodiments discussed above, the crushing part 56 further protrudes from the internal sheath 11 by increasing the rotation speed of the motor (not shown).

In accordance with the calculus crushing apparatus 55, when the rotation speed of the motor is increased, the centrifugal force applied to the head side of the crushing part with respect to the bending portion 58 increases; thus, it is possible to increase the outer diameter of the crushing part 56 with respect to the central axis C. Additionally, similar to the other embodiments, the shaft member 57 is pulled out from the internal sheath 11 so that the entire crushing part 56 further protrudes with respect to the internal sheath 11 so as to crush the calculus.

Sixth Embodiment

Figure 22:
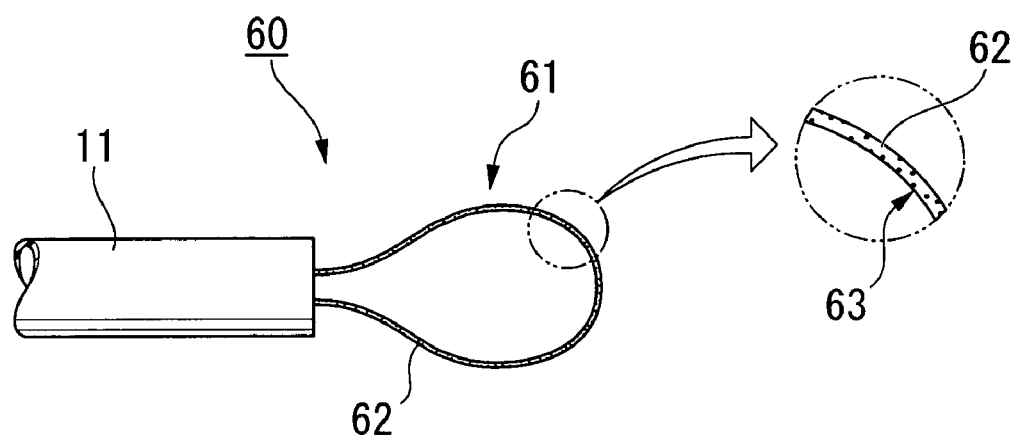
FIG. 22 is a plan view showing the crushing part of the calculus crushing apparatus of a sixth embodiment.
Figure 23:
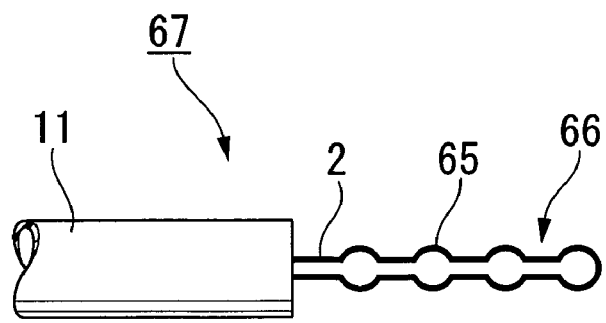
FIG. 23 is a plan view showing a variation of the crushing part of the calculus crushing apparatus of the sixth embodiment.

A sixth embodiment of the present invention will be explained with reference to the drawings. In comparison with the first embodiment, a calculus crushing apparatus 60 of the present embodiment has distinctive features (see FIG. 22) in which a crushing part 61 has a crushing wire 62, and an uneven pattern 63 is formed on the surface of the crushing wire 62. As shown in FIG. 23, a calculus crushing apparatus 67 may be employed, which has a crushing part 66 formed by reshaping the crushing wire 62 itself so as to produce an uneven pattern 65 consisting of alternating bent and straight portions. In addition, the crushing wire may consist of a plurality of thin single wires which are twisted, where uneven patterns are produced by twisting these single wires.

In accordance with the calculus crushing apparatus 60 or 67, frictional force generated by the crushing part 61 or 67 can be larger in comparison with the calculus crushing apparatus 1 of the first embodiment, and it is possible to further increase the cutting power when the crushing part 61 or 67 is put in contact with the calculus (not shown).

Seventh Embodiment

A seventh embodiment of the present invention will be explained with reference to the drawings. In comparison with the first embodiment, a calculus crushing apparatus 70 of the present embodiment has a distinctive feature of having a surrounding portion 71 which covers the basket part 6.

Figure 24:
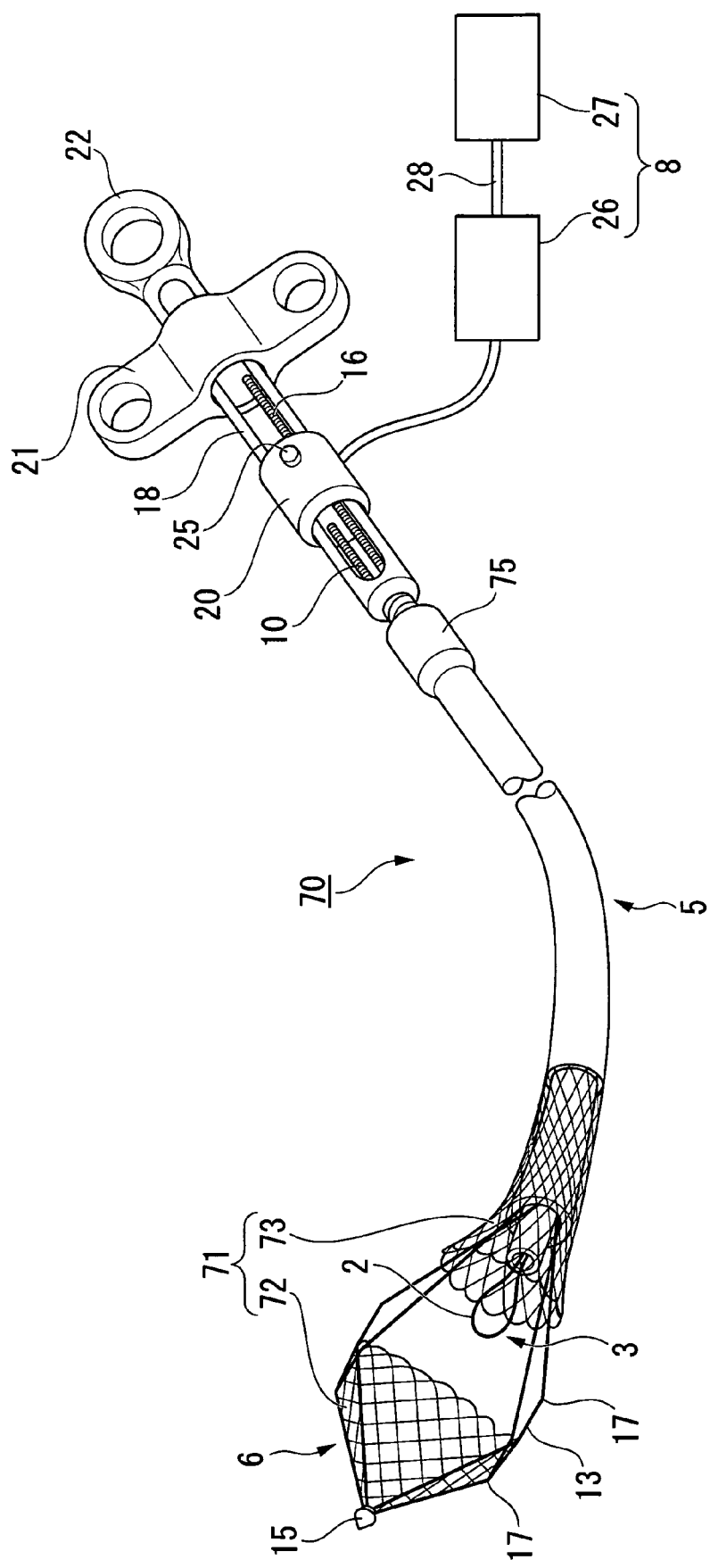
FIG. 24 is a diagram showing the general structure of a calculus crushing apparatus as a seventh embodiment.

As shown in FIG. 24, the surrounding portion 71 has (i) a first net part 72 with which an area defined from the head tip 15 of the basket wires 13 of the basket part 6 to the bending points 17 of each basket wire 13 which are closest to the head tip is covered, and (ii) a second net part 73 which is arranged between the outer sheath 12 and the internal sheath 11 in a freely slidable manner, and with which the crushing part 3 and a root portion of the basket part 6 are covered.

The first net part 72 is deployed together with the basket part 6 and is containable in the outer sheath 12. The head end of the second net part 73 has a bending shape formed by bending single wires. The base end of the second net part 73 is connected to a net pusher 75 which is arranged outside the outer sheath 12 in a freely slidable manner at a position ahead of the operation part main body 18. When the second net part 73 is protruded as far as possible from the outer sheath 12 by operating the net pusher 75, the head of the second net part 73 is put in contact with the base end of the first net part 72. The first net part 72 and the second net part 73 are not limited to so-called nets, and each may be formed by laser-cutting a pipe member so as to produce a net shape. The mesh size is preferably 0.5 to 3 mm. A net functioning as a cover, made of resin, may be applied to at least one of the first net part 72 and the second net part 73. In addition, the surface of at least one of the first net part 72 and the second net part 73 may be covered with a cover member made of resin (e.g., silicone).

The operation of the calculus crushing apparatus 70 of the present embodiment will be explained.

In addition to the steps performed in the medical procedure using the endoscope in the first embodiment, the medical procedure using an endoscope and this calculus crushing apparatus 70 further includes a step of holding the calculus CH using the surrounding portion 71, and a step of removing the calculus CH held by the surrounding portion 71 from the bile duct BD when the crushed calculus CH has a specific size.

Figure 25:
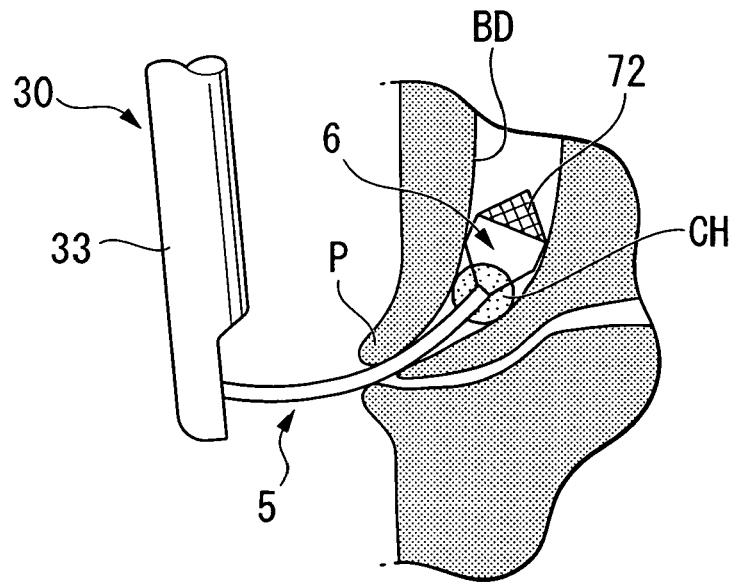
FIG. 25 is a plan view showing the crushing part of the calculus crushing apparatus of the seventh embodiment.

First, similar to the above-described other embodiments, the insertion part 33 of the endoscope 30 is inserted up to the vicinity of the duodenal papilla P, and the head of the insertion part 33 is positioned. Then, the sheath 5 is protruded from a channel (not shown) so as to insert the sheath from the duodenal papilla P into the bile duct BD. In this state, an operator (not shown) holds the holding slider 21, and advances the slider with respect to the operation part main body 18 while confirming the present state using an observation image. In this process, the basket part 6 protrudes from the head of the sheath 5 towards the inside of the bile duct BD and is deployed together with the first net part 72 (see FIG. 25).

Figure 26:
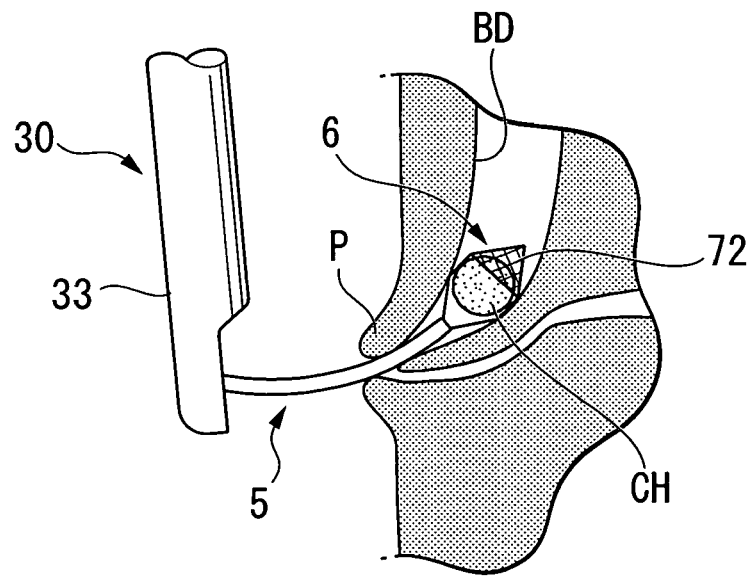
FIG. 26 is also a plan view showing the crushing part of the calculus crushing apparatus of the seventh embodiment.

The sheath 5 is then withdrawn to the base end side so as to catch the calculus CH on the head side of the deployed basket part 6 (see FIG. 26). The holding slider 21 is then withdrawn with respect to the operation part main body 18 so as to contract the basket part 6 and to support the calculus CH with respect to the sheath 5 while the head of the crushing part 3 contacts the calculus CH.

Figure 27:
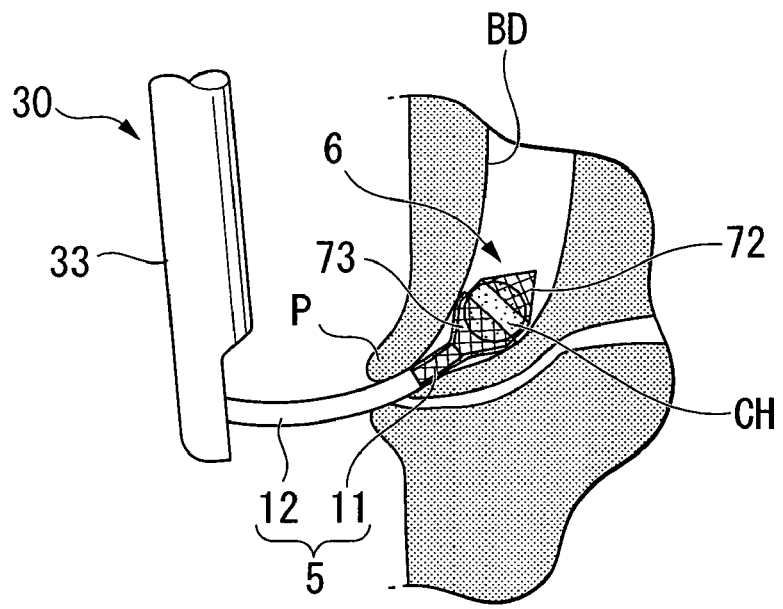
FIG. 27 is also a plan view showing the crushing part of the calculus crushing apparatus of the seventh embodiment.
Figure 28:
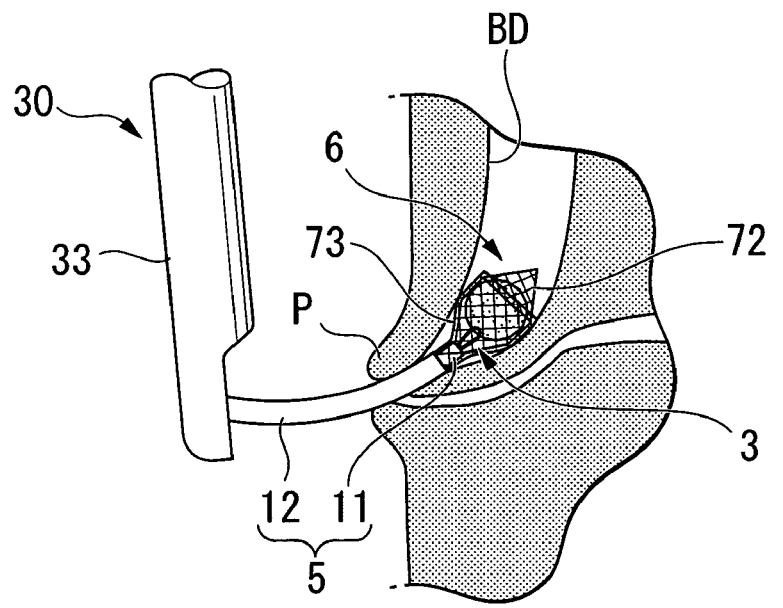
FIG. 28 is also a plan view showing the crushing part of the calculus crushing apparatus of the seventh embodiment.

Next, the net pusher 75 is operated so as to make the second net part 73 protrude from the head of the outer sheath 12, so that the root side of the basket part 6 is covered with the second net part 73 (see FIG. 27), and then the head of the second net part 73 is put in contact with the base end of the first net part 72 (see FIG. 28).

In this state, the motor 23 provided to the crushing part slider 20 is rotated so as to rotate the crushing part 3. Accordingly, the portion which the crushing part contacts is cut and crushed, similar to the above-described embodiments.

Even if crushed pieces of the calculus, which have a size larger than the mesh size, are scattered, such pieces are not scattered outside the mesh of the surrounding portion 71.

Figure 29:
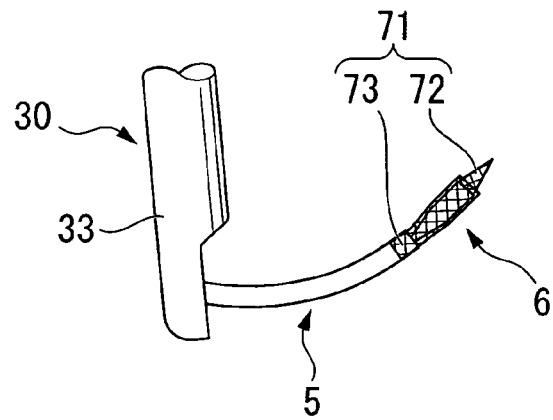
FIG. 29 is also a plan view showing the crushing part of the calculus crushing apparatus of the seventh embodiment.

After the calculus CH is divided into a plurality of calculus pieces (not shown), the rotation of the motor 23 is stopped and the crushing part slider 20 is withdrawn with respect to the operation part main body 18, so as to contain the crushing part 3 in the internal sheath 11. Simultaneously, the holding slider 21 is withdrawn with respect to the operation part main body 18 so as to contract the basket part 6 and hold the calculus pieces inside the surrounding portion 71 (see FIG. 29). The calculus pieces are removed from the bile duct BD and collected.

Figure 30:
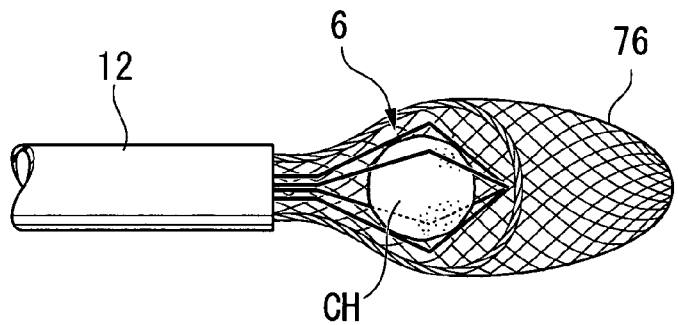
FIG. 30 is also a plan view showing a variation of the surrounding portion of the calculus crushing apparatus of the seventh embodiment.
Figure 31:
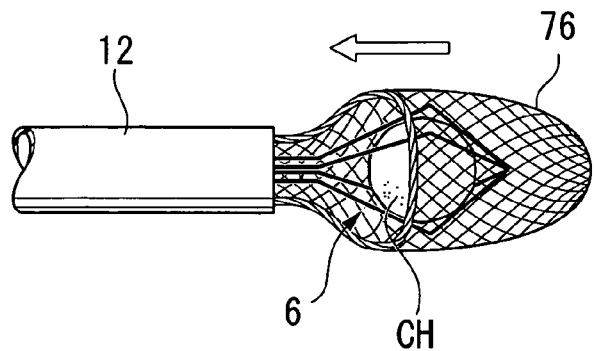
FIG. 31 is a diagram explaining an example of use of the variation of the surrounding portion of the calculus crushing apparatus of the seventh embodiment.

In accordance with the calculus crushing apparatus 70, it is possible to preferably prevent the calculus CH from being scattered outside the basket part 6, and thus more preferably collect the calculus CH from the bile duct BD. In particular, the surrounding portion 71 has a net shape; thus, the cutting state inside the surrounding portion 71 can be visually observed. Additionally, as shown in FIG. 30, a surrounding portion 76 having a bag shape may be used so as to cover the whole basket part 6. In this case, the surrounding portion 76 reaches a position ahead of the basket part 6, and a net slider (not shown) is operated so as to cover the basket part 6 together with the calculus CH from the head side thereof (see FIG. 31). Also in this case, functions and effects similar to those explained above can be obtained.

Eighth Embodiment

Figure 32:
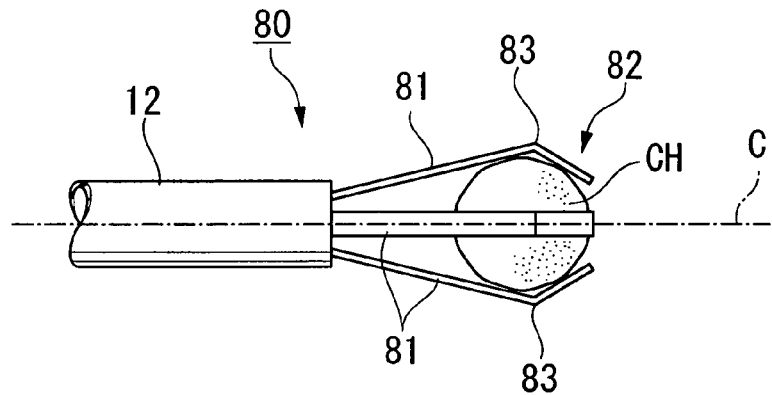
FIG. 32 is a plan view showing the holding part of the calculus crushing apparatus of an eighth embodiment.

An eighth embodiment of the present invention will be explained with reference to the drawings. In comparison with the first embodiment, a calculus crushing apparatus 80 of the present embodiment has a distinctive feature (see FIG. 32) of employing a holding part 82 consisting of a plurality of arms 82 for holding the calculus CH, instead of the basket part 6.

Each arm 81 extends from the head of the outer sheath 12 so as to be away from the central axis C and to produce a specific angle between the arm 81 and the central axis C. Each arm is also bent at a bending portion 83 toward the central axis C.

In accordance with the calculus crushing apparatus 80, the calculus CH can be preferably held by the holding part 82 by closing the arms 81; thus, functions and effects similar to the first embodiment can be obtained.

Ninth Embodiment

Figure 33:
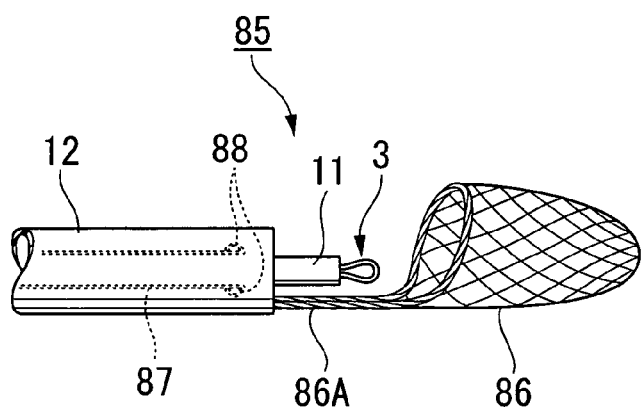
FIG. 33 is a plan view showing the holding part of the calculus crushing apparatus of a ninth embodiment.

A ninth embodiment of the present invention will be explained with reference to the drawings. In comparison with the first embodiment, a calculus crushing apparatus 85 of the present embodiment has distinctive features (see FIG. 33) of omitting the basket part 6, and instead employing a holding part which includes (i) a bag portion 86 like a net, which can freely protrude from and withdraw inside the outer sheath 12, and can also be deployed or folded, and (ii) support parts 87 for supporting the bag portion 86 by pushing the deployed bag portion 86 from the inside thereof in outward radial directions.

The bag portion 86 is connected to a holding operation wire and a holding slider (both not shown) via a joint part 86A. Each support part 87 has a wire form, and the plurality of the support parts 87 is arranged in a freely slidable manner inside the outer sheath 12 and is connected via support operation wires (not shown) to a support slider provided to an operation part (not shown). The head of each support part 87 has a head ring portion 88 contributing to easy movement inside the bag portion 86.

The operation of the calculus crushing apparatus 85 of the present embodiment will be explained.

First, similar to the above-described other embodiments, the sheath 5 of the calculus crushing apparatus 85 is inserted from the duodenal papilla (not shown) to the bile duct. Then the holding slider (not shown) is advanced with respect to an operation part main body (not shown), so as to arrange the bag portion 86 at a position ahead of the crushing part 3 by a specific distance. The holding slider is then withdrawn to the base end side so as to catch and contain a calculus (not shown) inside the bag portion 86.

Figure 34:
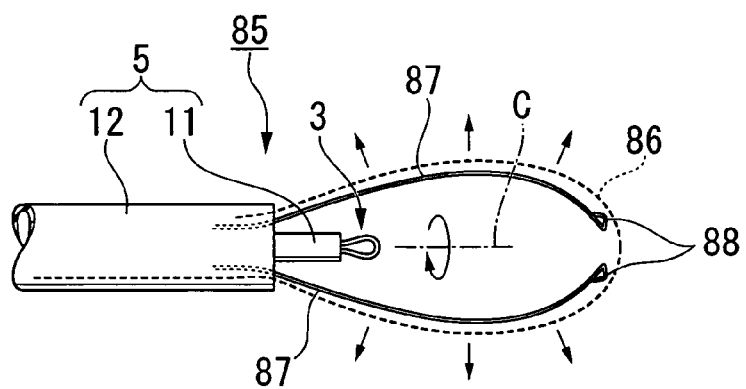
FIG. 34 is a plan view showing main portions of the calculus crushing apparatus of the ninth embodiment.

Next, the support slider (not shown) is advanced with respect to the operation part main body so that the head sides of the support parts 87 protrude from the internal sheath 11 and slide inside the bag portion 86 up to the head of the bag portion 86, thereby pushing the bag portion 86 in outward radial directions (see FIG. 34). In this state, the calculus is supported in the bag portion 86, and a motor (not shown) is operated so as to rotate a crushing part operating wire (not shown) around the axis, thereby rotating the crushing part 3.

In accordance with the calculus crushing apparatus 85, the calculus is held using the bag portion 86; thus, it is possible to more reliably hold the calculus in comparison with the basket part 6. In addition, the bag portion 86 is supported from the inside thereof by using the support parts 87; thus, it is possible to maintain the shape of the bag portion 86 and to preferably prevent the bag portion 86 from twisting.

The technical range of the present invention is not limited to the above-described embodiments, and various variations are possible within the scope and spirit of the present invention.

Figure 35:
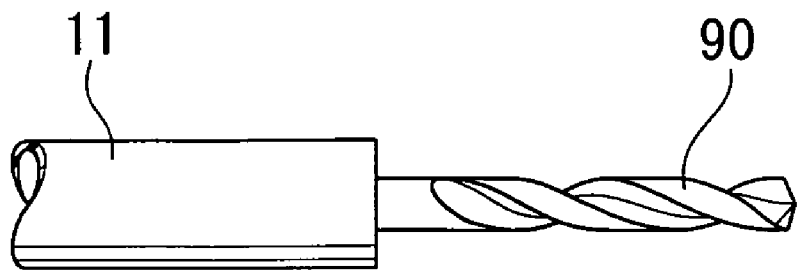
FIG. 35 is a plan view showing a variation of the crushing part of the calculus crushing apparatus of the first embodiment.
Figure 36:
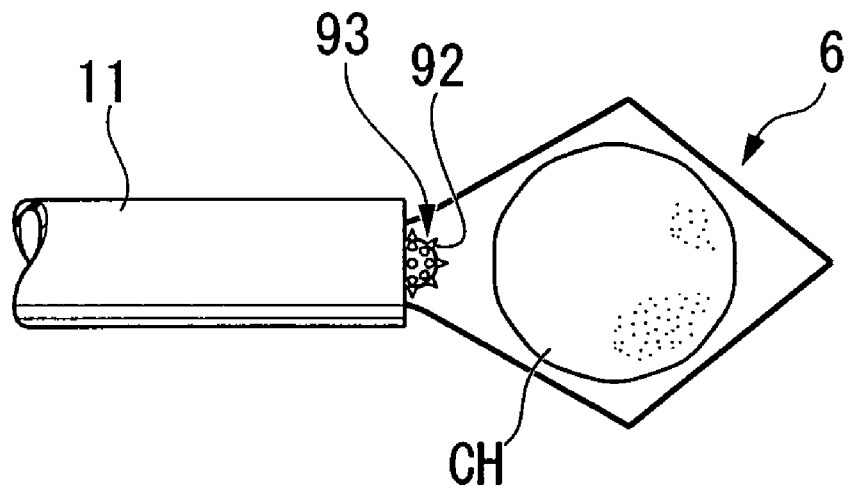
FIG. 36 is a plan view showing main portions of a variation of the calculus crushing apparatus of the first embodiment.

For example, in the above-described embodiments, a wire-shaped crushing part is rotated; however, as shown in FIG. 35, a drill 90 may be protruded and rotated. Additionally, as shown in FIG. 36, a crushing part 93 having a plurality of pointed protrusions 92 at the head thereof may be rotated while it contacts the calculus CH held by the basket part 6, so as to crush the calculus CH.

Figure 37:
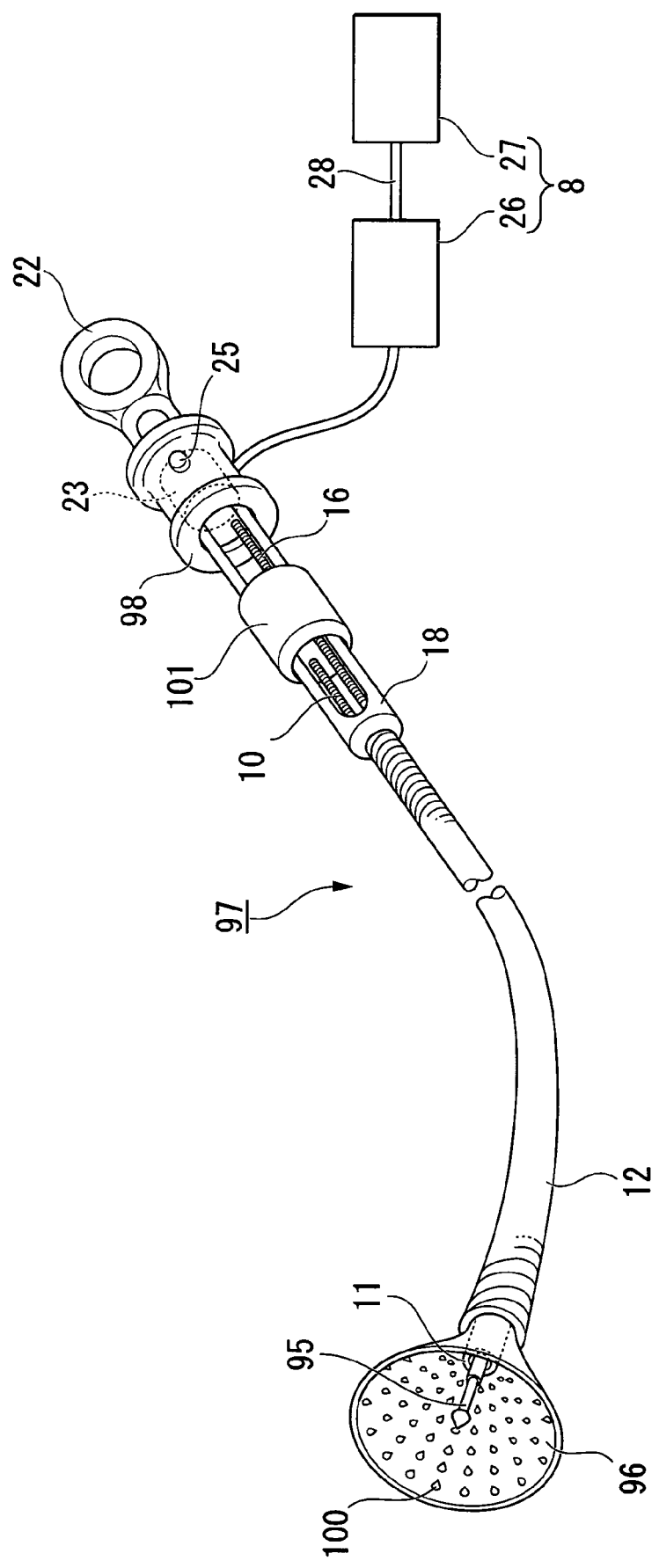
FIG. 37 is a diagram showing the general structure of a variation of the calculus crushing apparatus.

Below, a calculus crushing apparatus 97 will be explained (see FIG. 37) in which (i) instead of the crushing part employed in the above-described embodiments, a holding part 95 is arranged in a slidable manner with respect to the internal sheath 11, and (ii) instead of the holding part of the above embodiments, a crushing part 96 is arranged in a slidable manner with respect to the outer sheath 12.

The head portion of the holding part 95 of the calculus crushing apparatus 97 has a sagittate form, and thus cannot be pulled out after the calculus is stabbed with this head portion. The holding part 95 is connected to the holding operation wire 16 arranged inside the internal sheath 11. The holding operation wire 16 is arranged in a freely slidable manner with respect to the operation part main body 18 and is connected to a holding slider 98 in which the motor 23 and the hand switch 25 for rotating the holding operation wire 16 are provided.

The crushing part 96 has a conical shape which opens toward the head side, and can be expanded or folded by advancing or withdrawing the crushing part operating wire 10 along the outer sheath 12. A plurality of pointed protrusions 100 is formed on the inner face of the crushing part 96, so as to cut the calculus. The crushing part operating wire 10 is connected to a crushing part slider 101 which is arranged in a freely slidable manner with respect to the operation part main body 18.

The operation of the calculus crushing apparatus 97 will be explained.

Figure 38:
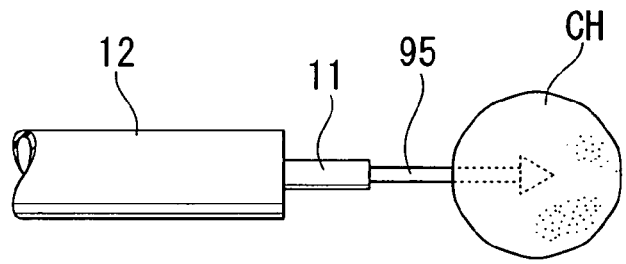
FIG. 38 is a diagram explaining an example of use of the calculus crushing apparatus shown in FIG. 37.

After the sheath 5 is inserted into a bile duct (not shown), the holding slider 98 is advanced with respect to the operation part main body 18, so that the head portion of the holding part 95 is protruded from the internal sheath 11 and the calculus CH is stabbed with this head portion (see FIG. 38). Next, the hand switch 25 is turned on so as to operate the motor 23 and rotate the holding operation wire 16. Simultaneously, the holding part 95 and the calculus CH are rotated.

Figure 39:
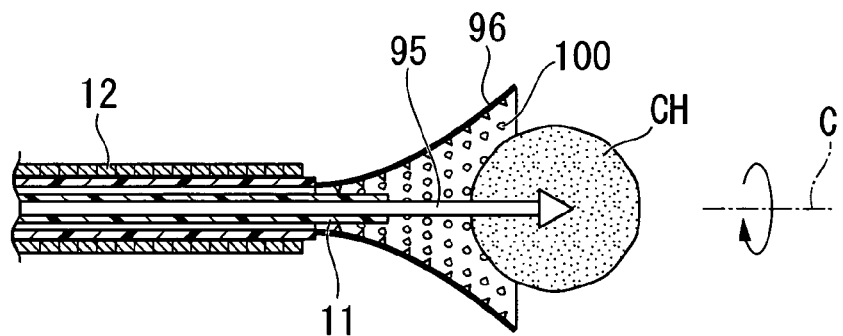
FIG. 39 is also a diagram explaining the example of use of the calculus crushing apparatus shown in FIG. 37.
Figure 40:
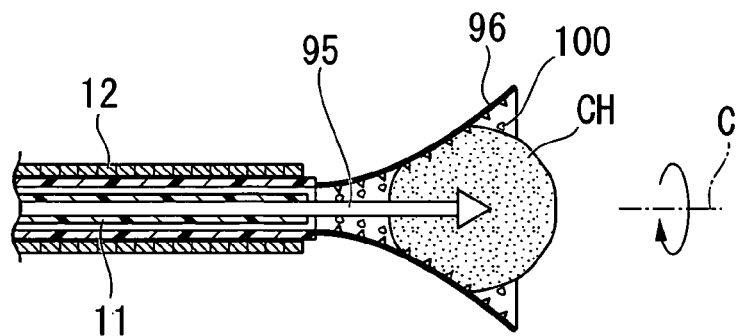
FIG. 40 is also a diagram explaining the example of use of the calculus crushing apparatus shown in FIG. 37.

In this state, the crushing part slider 101 is advanced with respect to the operation part main body 18 so that the crushing part 96 is protruded from the outer sheath 12, together with the crushing part operating wire 10. In this process, as shown in FIG. 39, the head side of the crushing part 96 is opened in outward radius directions in a manner such that the diameter of the head side is considerably larger than that of the calculus CH. In the next step, the crushing part slider 101 is withdrawn with respect to the operation part main body 18 so that the inner face of the crushing part 96 is pushed onto the calculus (see FIG. 40). In this process, the calculus CH is cut and crushed by the pointed protrusions 100 formed on the inner face of the crushing part 96.

Therefore, as the crushing part slider 101 is withdrawn, the calculus CH is also cut into fine pieces by the crushing part 96. During this process, the cut pieces may be suctioned into the sheath 5 using a suction source (not shown).

Figure 41:
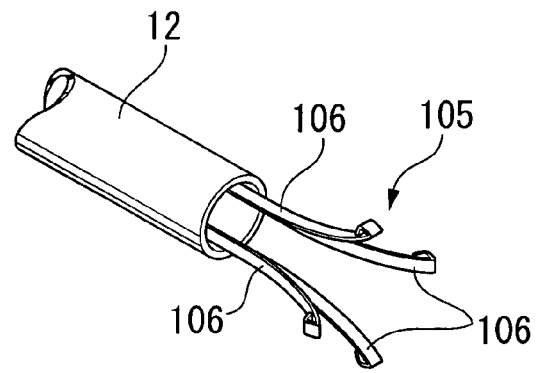
FIG. 41 is a perspective view showing main portions of a variation of the calculus crushing apparatus shown in FIG. 37.
Figure 42:
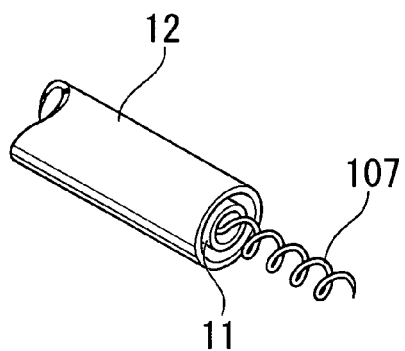
FIG. 42 is a perspective view showing main portions of another variation of the calculus crushing apparatus shown in FIG. 37.
Figure 43:
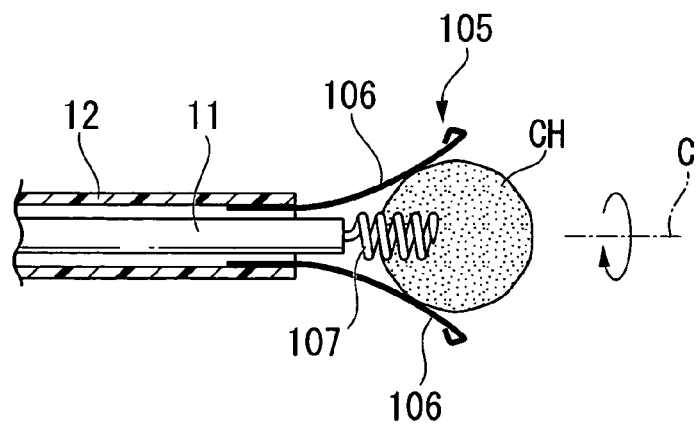
FIG. 43 is a diagram explaining an example of use of the calculus crushing apparatus shown in FIGS. 41 and 42.

In addition, as shown in FIG. 41, a crushing part 105 may be employed, which consists of four linear and flexible arms 106 which are combined and contained in the outer sheath 12 and whose heads are bent outward in radial directions. On the other hand, a holding part 107 (see FIG. 42) may be employed, which has a spiral form and can be freely protruded from or withdrawn into the internal sheath 11. In this case, as shown in FIG. 43, the calculus CH is cut and crushed by the crushing part 105 by rotating the holding part 107 with respect to the internal sheath 11.

Figure 44:
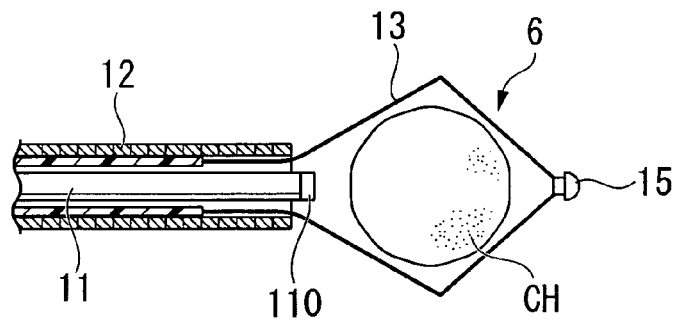
FIG. 44 is a diagram showing the general structure of another variation of the calculus crushing apparatus.

Additionally, as shown in FIG. 44, an energy emitting part 110 (i.e., a crushing part) for emitting ultrasonic waves may be provided. In this case, the energy emerging part 110 is connected to an energy transmitting part (not shown) which is provided inside the internal sheath 11 in a freely slidable manner. The energy emitted from the energy emitting part 110 may apply mechanical impact waves to the calculus, or apply water pressure due to electrohydraulic lithotripsy.

Figure 45:
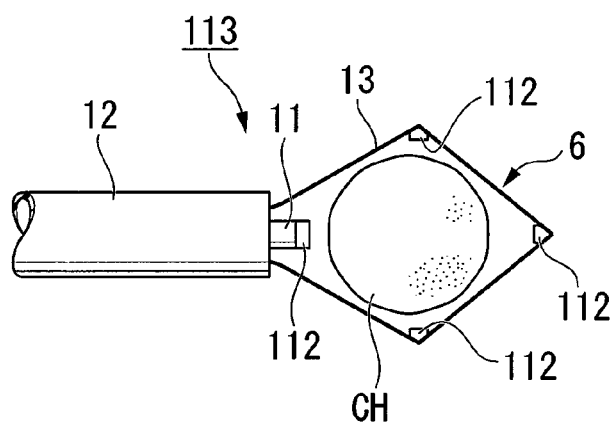
FIG. 45 is a diagram showing the general structure of another variation of the calculus crushing apparatus.

In addition, as shown in FIG. 45, a calculus crushing apparatus 113 may be provided in which a plurality of electrodes 112 are attached not only to a head portion of an energy transmitting part but also to the bending points 17 of the basket part 6 and the head tip 15. In this case, the above-described energy emitting part may be substituted for each electrode 112.

Figure 46:
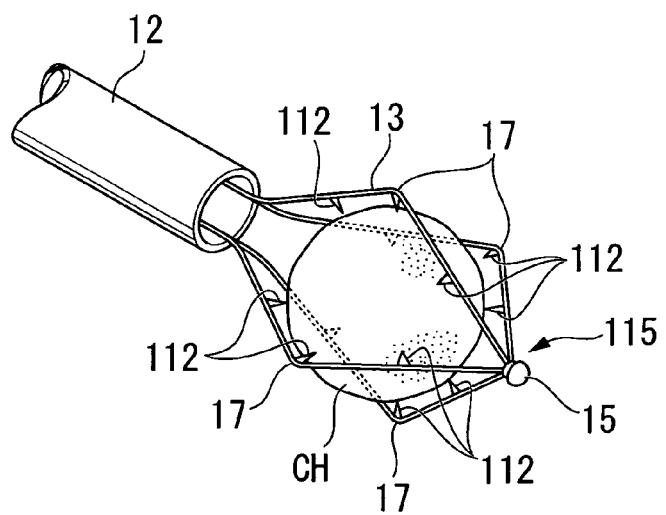
FIG. 46 is a diagram showing the general structure of another variation of the calculus crushing apparatus.

Furthermore, as shown in FIG. 46, the plurality of electrodes 112 may also be attached not only to the bending points 17 of a basket part 115 but also on the middle of each basket wire 13.

The invention claimed is:

1. An apparatus for crushing a calculus, the apparatus comprising:
   a holding part adapted to surround and catch the calculus so as to fixedly hold and support the calculus;
   a crushing part which has a first end, a second end, and a head portion comprising an empty loop shape which is surrounded by the holding part, the crushing part being adapted to rotate and crush the calculus supported by the holding part;
   a sheath for containing the crushing part in a manner such that the first and second ends extend through the sheath and that the head portion of the crushing part is protrudable from a head of the sheath; and
   a rotation input part for rotating the crushing part and adjusting a rotation speed, thereof to vary a centrifugal force applied to the head portion of the crushing part so as to adjust an amount of protrusion of the crushing part measured from the head of the sheath to the head portion of the crushing part, wherein
   a radius of rotation of the crushing part with respect to a rotation axis thereof increases or decreases in accordance with an increase or decrease in the rotation speed of the crushing part; and
   the head portion of the crushing part is adapted to move relative to the holding part in a direction along the rotation axis.

2. An apparatus in accordance with claim 1, wherein the radius of rotation of the crushing part is perpendicular to the central axis.

3. An apparatus in accordance with claim 1, wherein the holding part has a basket shape.

4. An apparatus in accordance with claim 1, wherein the crushing part is made of metal.

5. An apparatus in accordance with claim 4, wherein the crushing part also includes resin.

6. An apparatus in accordance with claim 1, wherein the holding part supports the calculus in a manner such that the head portion of the crushing part contacts the calculus.

7. An apparatus in accordance with claim 1, further comprising:
   an operation part for making the crushing part be advanced or withdrawn with respect to the sheath.

8. An apparatus in accordance with claim 1, wherein the rotation input part rotates the crushing part to adjust the amount of protrusion of the crushing part and to advance or withdraw the crushing part within the holding part.

9. A medical procedure using an endoscope, the medical procedure comprising the steps of:
   inserting a sheath from a duodenal papilla into a bile or pancreatic duct, wherein the sheath contains a crushing part which has a first end, a second end, and a head portion comprising an empty loop shape, is protrudable from a head of the sheath, and rotates so as to cut a calculus in the bile or pancreatic duct;
   inserting the head of the sheath up to a position where the calculus can be held in the bile or pancreatic duct;
   holding the calculus using a holding part which surrounds and catches the calculus so as to fixedly hold and support the calculus; and
   crushing the calculus supported by the holding part by using the crushing part which is also surrounded by the holding part, by rotating the crushing part and adjusting a rotation speed thereof to vary a centrifugal force applied to the head portion of the crushing part so as to adjust an amount of protrusion of the crushing part measured from the head of the sheath to the head portion of the crushing part, wherein:

a radius of rotation of the crushing part with respect to a rotation axis thereof increases or decreases in accordance with an increase or decrease in the rotation speed of the crushing part, and the head portion of the crushing part is adapted to move relative to the holding part in a direction along the rotation axis.

10. A medical procedure in accordance with claim 9, further comprising the step of:

holding the calculus using a surrounding portion with which the holding part is covered.

11. A medical procedure in accordance with claim 10, further comprising the step of:

removing the calculus held by the surrounding portion from the bile or pancreatic duct.

12. A medical procedure in accordance with claim 9, further comprising the step of:

collecting the calculus using a collecting device.

13. A medical procedure in accordance with claim 9, wherein the holding part supports the calculus in a manner such that the head of the crushing part contacts the calculus.

14. A medical procedure in accordance with claim 9, further comprising the step of:

making the crushing part be advanced or withdrawn with respect to the sheath by using an operation part.

15. A medical procedure in accordance with claim 9, wherein the crushing part is rotated to adjust the amount of protrusion of the crushing part and to advance or withdraw the crushing part within the holding part.

* * * * *